United States Patent [19]

Dessau et al.

[11] Patent Number: 5,316,661

[45] Date of Patent: May 31, 1994

[54] PROCESSES FOR CONVERTING FEEDSTOCK ORGANIC COMPOUNDS

[75] Inventors: Ralph M. Dessau, Edison, N.J.; Robert K. Grasselli, Chadds Ford; Rudolph M. Lago, Yardley, both of Pa.; John G. Tsikoyiannis, Princeton, N.J.

[73] Assignee: Mobil Oil Corporation, Fairfax, Va.

[21] Appl. No.: 47,137

[22] Filed: Apr. 16, 1993

Related U.S. Application Data

[63] Continuation-in-part of Ser. No. 910,861, Jul. 8, 1992.

[51] Int. Cl.$^5$ ............................................. C07C 5/333
[52] U.S. Cl. ......................................... 208/46; 585/661
[58] Field of Search ................ 585/660, 661; 288/46; 502/64

[56] References Cited

U.S. PATENT DOCUMENTS

| | | | |
|---|---|---|---|
| Re. 28,341 | 2/1975 | Wadlinger et al. | 208/120 |
| Re. 29,948 | 3/1979 | Dwyer et al. | 208/110 |
| 3,308,069 | 5/1967 | Wadlinger et al. | 252/455 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 3,941,871 | 3/1976 | Dwyer et al. | 423/326 |
| 4,016,245 | 4/1977 | Plank et al. | 423/328 |
| 4,046,859 | 9/1977 | Plank et al. | 423/328 |
| 4,076,842 | 2/1978 | Plank et al. | 423/328 |
| 4,229,424 | 10/1980 | Kokotailo | 423/328 |
| 4,397,827 | 8/1983 | Chu | 423/326 |
| 4,556,477 | 12/1985 | Dwyer | 208/111 |
| 4,593,137 | 6/1986 | Fraenkel et al. | 585/467 |
| 4,615,995 | 10/1986 | Le Van Mao | 502/64 |
| 4,699,892 | 10/1987 | Suzuki | 502/4 |
| 4,771,029 | 9/1988 | Pereira et al. | 502/355 |
| 4,778,665 | 10/1988 | Krishnamurthy et al. | 423/239 |
| 4,800,187 | 1/1989 | Lachman et al. | 502/64 |
| 4,970,183 | 11/1990 | Nakamoto et al. | 502/68 |
| 4,973,399 | 11/1990 | Green et al. | 502/67 |
| 5,019,263 | 5/1991 | Haag et al. | 210/500.25 |
| 5,023,220 | 6/1991 | Dight et al. | 502/65 |
| 5,145,659 | 9/1992 | McWilliams | 423/328 |

OTHER PUBLICATIONS

Lachman et al., "Extruded Monolithic Catalyst Supports," Symposium on Catalyst Supports: Chemistry, Forming and Characteristics, American Chemical Society Meeting, New York City, Aug., 1991.

Sano, T., et al., "Preparation and Characterization of ZSM-5 Zeolite Film," Zeolites, 11, 842–845 (1991).

Sano, T., et al., "New Preparation Method for Highly Siliceous Zeolite Films," J. Mater. Chem., 2, 141–142 (1992).

Bosh, et al., "Catalytic Reduction of Nitrogen Oxides," Catalysts Today, 2, 369–401, 489–531 (1987).

*Primary Examiner*—Anthony McFarlane
*Attorney, Agent, or Firm*—A. J. McKillop; D. P. Santini

[57] ABSTRACT

A method for synthesizing a zeolite bonded to a substrate utilizes a reaction mixture having a $H_2O/YO_2$ molar ratio of at least 25 and Y is a tetravalent element, particularly silicon.

A structure made according to this method includes a film of interconnected zeolite crystals bonded to a substrate and the structure is characterized by a value r representing the mg of zeolite/$cm^2$ of substrate surface and a value e representing the coating efficiency as mg of bonded zeolite/mg of $YO_2$ initially in the synthesis mixture; wherein r is at least 0.5 and e is at least 0.05.

Processes are provided for separation, sorption, organic feedstock conversion, light paraffin dehydrogenation and $NO_X$ conversion over the structure.

16 Claims, 2 Drawing Sheets

PROCESSES FOR CONVERTING FEEDSTOCK ORGANIC COMPOUNDS

CROSS-REFERENCE TO RELATED APPLICATIONS

This application is a continuation-in-part, of application Ser. No. 07/910,861, filed Jul. 8, 1992, which is incorporated herein in its entirety by reference.

FIELD OF THE INVENTION

The invention is a method for synthesizing films of zeolites which are bonded to substrates and the structures made by this method. The structures may be used for separations, for the sorption of hydrocarbons, for catalysis, for paraffin dehydrogenation and for Selective Catalytic Reduction (SCR) of $NO_x$.

BACKGROUND OF THE INVENTION

Synthetic zeolites have been used as adsorptive separation agents for gases and liquids, and as catalysts. Generally, zeolites have been synthesized to yield a powder form of the crystalline material which can be formed or extruded into granules, beads or pellets, often incorporated with a binder such as clay or alumina.

Zeolites both natural and synthetic, include a wide variety of positive ion-containing crystalline aluminosilicates. These aluminosilicates can be described as a rigid three-dimensional framework of $SiO_4$ and $AlO_4$ in which the tetrahedra are crosslinked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as $Ca/2$, $Sr/2$, $Na$, $K$ or $Li$, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolite have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); ZSM-35 (U.S. Pat. No. 4,016,245); ZSM-38 (U.S. Pat. No. 4,046,859); and zeolite ZSM-23 (U.S. Pat. No. 4,076,842), merely to name a few.

The $SiO_2/Al_2O_3$ mole ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to infinity. U.S. Pat. No. 3,941,871 (U.S. Pat. No. Re. 29,948) discloses a porous crystalline silicate made from a reaction mixture containing no deliberately added aluminum in the synthesis mixture and exhibiting the X-ray diffraction pattern characteristics of ZSM-5 type zeolites. U.S. Pat. Nos. 4,061,724; 4,073,865; and 4,104,294 describe crystalline silicates or organosilicates of varying alumina and metal content.

Although zeolites include materials containing silicon and aluminum, it is recognized that the silicon and aluminum atoms may be replaced in whole or in part with other elements. More particularly, Ge is an art recognized substitute for Si and B, Cr, Fe, and Ga are art recognized replacements for Al. Accordingly, the term zeolite as used herein shall connote not only materials containing silicon and, optionally, aluminum atoms in the crystalline lattice structure thereof, but also materials which contain suitable replacement atoms for such silicon and/or aluminum.

Monolithic substrates such as wash coated ceramics, described for example in U.S. Pat. No. 4,771,029, and extruded catalytic monoliths, described for example by Lachman et al., "Extruded Monolithic Catalyst Supports", *Symposium on Catalyst Supports: Chemistry, Forming and Characteristics*, American Chemical Society, New York City Meeting, Aug. 1991, 535–543, have been described as useful in emissions control.

U.S. Pat. No. 4,800,187 describes a method for crystallizing a zeolite on the surface of a ceramic monolith containing silica with a crystallization mixture containing a ratio of $H_2O/SiO_2$ of 16–20 to one and a ratio of $SiO_2/AlO_3$ of one to 0.0–0.4 for the synthesis of ZSM-5. Different ratios are described for large pore zeolites X and Y.

However, when well known zeolite synthesis techniques are used in an attempt to obtain crystallization of a zeolite film adherent to a substrate, there is a strong tendency for homogeneous crystallization to occur. That is, the crystals form in the crystallization solution and settle to the bottom to yield a powder form rather than bonding to the surface to form a strongly adherent film.

It is therefore an object of the invention to provide a method for synthesizing a zeolite film of continuously intergrown zeolite crystals strongly bonded to the surface of a substrate or monolith.

It is another object of the invention to provide a structure synthesized by this method the structure having numerous applications for sorption, hydrocarbon conversions, paraffin dehydrogenation, and catalytic conversion of $NO_X$.

SUMMARY OF THE INVENTION

Accordingly, a method is provided for synthesizing an intermediate pore zeolite film bonded to a substrate. A chemical mixture capable of forming the zeolite is prepared wherein the mixture comprises a $H_2O/YO_2$ molar ratio of at least 25, Y comprising a tetravalent element, and a substrate is contacted with the mixture under crystallization conditions characterized by a value d wherein d = the ratio of $YO_2$ content of the chemical synthesis mixture to substrate superficial surface area in $mg/cm^2$; and d is at least about 0.5 and less than about 200; preferably about 2–50;

so that an essentially continuous layer of zeolite forms as bonded to the substrate. Y is preferably silicon, germanium or titanium.

A structure prepared according to this method comprises a film of interconnected zeolite crystals bonded to a substrate surface. The structure is characterized by a value r representing an amount of zeolite bonded to the substrate expressed as mg of zeolite/cm$^2$ of substrate surface, and r is at least about 0.5: preferably from about 1 to about 50.

The coating efficiency, e, expressed as mg of zeolite bonded to the substrate/mg of $YO_2$ initially present in the synthesis mixture may be calculated according to the formula: e=r/d. Accordingly to the method described, e is at least about 0.05, preferably at least about 0.1 and can reach values close to 1.

A process is also provided for sorption of at least one component from a mixture of components having different sorption characteristics with respect to the inventive structure described above. The mixture is contacted with a catalytically inactive form of the structure to selectively sorb at least one component of the mixture.

A process is also provided for sorption and retention of hydrocarbons contained in exhaust gases. It involves contacting the gas with the structure at low temperature, such as during the startup period of an internal combustion engine, and removing the hydrocarbons from the exhaust gas prior to releasing it to the atmosphere.

A process is also provided for converting feedstock organic compounds to conversion product by contacting the feedstock, under catalytic conversion conditions, with a reaction zone comprising a catalytically active structure described above with passage of conversion reactants through the structures so that an effluent emerging from the structure contains at least one conversion product.

A process is also provided for dehydrogenation of a light paraffin feedstock by contacting the light paraffin feedstock under dehydrogenation conditions with a reaction zone comprising a catalytically active structure described above with passage of conversion reactants through the structures so that an effluent emerging from the structure contains at least on dehydrogenation product.

A process for effecting catalytic conversion of $NO_x$ in exhaust gases is also provided and involves mixing the exhaust gas with suitable reducing agent at up to 200° C. with a sufficient amount of reducing agent for reduction of $NO_x$, and contacting the mixture with an active form of the inventive structure at a temperature from about 200° C. to about 600° C. Suitable reducing agents are hydrogen, CO, nitrogen containing entities such as ammonia, hydrogen cyanide, urea and cyanuric acid, oxygenates including methanol, ethanol, propanol, formaldehyde, acetaldehyde, acetone and methyl ethyl ketone and hydrocarbons including $C_2$-$C_4$ paraffins and olefins.

Advantageously, the zeolite film is strongly bonded to the surface of a substrate so that the mechanical integrity of the film is maintained when the structure is exposed to high flow rates of gases or liquids, as is often required in a variety of sorption and catalytic applications.

The film is also advantageously used in a variety of applications.

DESCRIPTION OF THE PREFERRED EMBODIMENTS

Under certain conditions, crystallization of zeolites can be directed almost exclusively onto the surface of substrates and homogeneous crystallization can be avoided. In homogeneous crystallization, homogeneously nucleated crystals form as discrete solid particles in the liquid synthesis medium and settle, due to gravity, on the bottom of the crystallization vessel rather than adhering to a substrate.

Using the method of the invention, a zeolite film is synthesized as bonded to a substrate. "Bonded" is intended to mean that the film is strongly adherent to the surface of a substrate and remains substantially adherent when subjected to conditions of catalysis, adsorption and separation, particularly high flow-through of gases and liquids. The film consists of an array of substantially continuously intergrown crystals which are connected to each other. This intergrowth is important for the mechanical integrity of the film.

Figure 1:
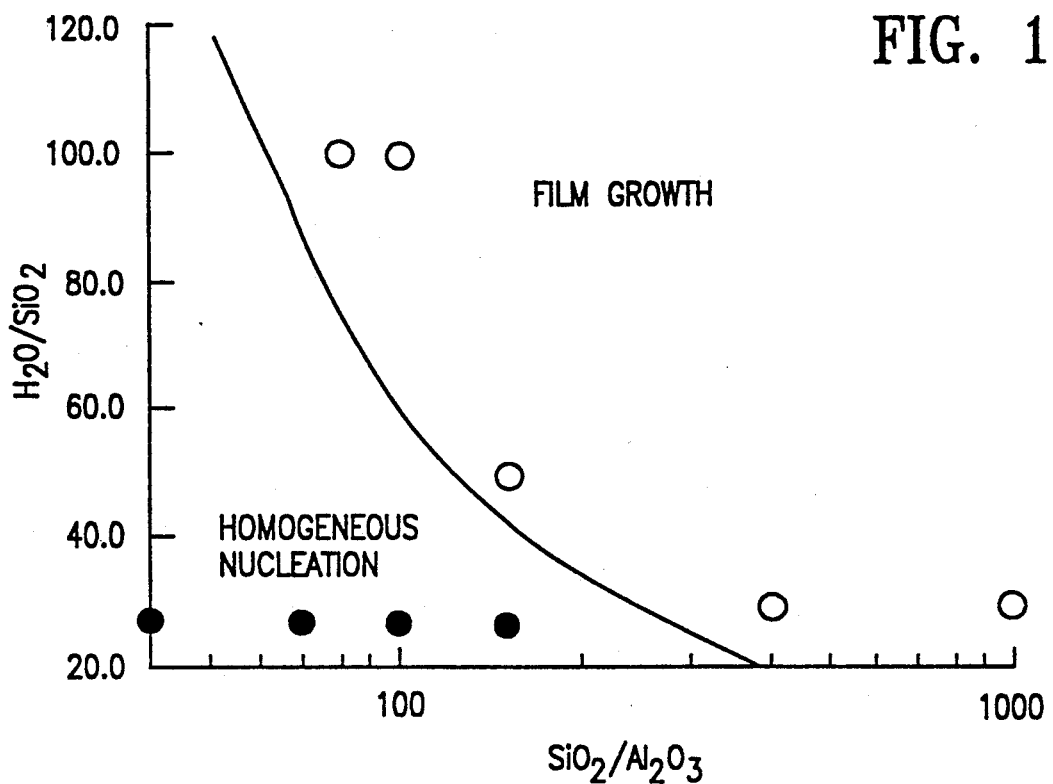
FIG. 1 is a graph demonstrating molar ratios of synthesis components for film growth.

In order to synthesize the film of the invention, the composition of the crystallization reaction mixture has a minimum $H_2O/YO_2$ molar ratio, as calculated by conventional methods, which increases as the reaction mixture $YO_2/X_2O_3$ molar ratio decreases, Y being a tetravalent element, preferably silicon, germanium or titanium, and X being a trivalent element, preferably aluminum, iron, boron or gallium. For example, as shown in FIG. 1, in the reaction mixture,

| $SiO_2/Al_2O_3$ | and | $H_2O/SiO_2$ |
|---|---|---|
| 1000 | | 28 |
| 400 | | 30 |
| 150 | | 50 |
| 80 | | 100 | crystallization occurs substantially on the substrate surface and homogeneous nucleation is minimized. However, if

| $SiO_2/Al_2O_3$ | and | $H_2O/SiO_2$ |
|---|---|---|
| 150 | | 28 |
| 100 | | 28 |
| 80 | | 28 |
| 50 | | 28 | substantial homogeneous nucleation leading to powder occurs with very little amount of zeolite adherent on the substrate.

For maximum coating efficiency, when the $YO_2/X_2O_3$ ratio in the reaction mixture is greater than about 400, the $H_2O/YO_2$ in the reaction mixture is at least about 25. When the $YO_2/X_2O_3$ is greater than about 150 and less than about 400, the $H_2O/YO_2$ is at least about 35. When the $YO_2/X_2O_3$ is less than about 150, the $H_2O/YO_2$ is at least about 45.

Accordingly, the crystallization mixture has a composition in terms of mole ratios including:

| $H_2O/YO_2$ | 25 to 500 |
| --- | --- |
| $YO_2/X_2O_3$ | 26 to ∞ |
| $OH^-/YO_2$ | 0.01 to 0.8 | wherein X is a trivalent element and Y is a tetravalent element.

A preferred crystallization mixture includes:

| $H_2O/YO_2$ | 30 to 200 |
| --- | --- |
| $YO_2/X_2O_3$ | 40 to ∞ |
| $OH^-/YO_2$ | 0.02 to 0.4 |

A more preferred crystallization mixture includes:

| $H_2O/YO_2$ | 30 to 150 |
| --- | --- |
| $YO_2/X_2O_3$ | 50 to ∞ |
| $OH^-/YO_2$ | 0.02 to 0.4 |

Typical zeolites to be synthesized according to the invention are characterized by a Constraint Index of about 1 to about 12. The Constraint Index is a convenient measure of the extent to which a zeolite provides constrained access to molecules of varying sizes to its internal structure. The method by which Constraint Index is determined is described fully in U.S. Pat. No. 4,016,218, incorporated herein by reference for details of the method.

Zeolites which conform to the specified values of Constraint Index for medium pore zeolites include ZSM-5, ZSM-11, ZSM-12, ZSM-22, ZSM-23, ZSM-35, ZSM-38, ZSM-5/ZSM-11 intermediate, and ZSM-48, i.e., particularly zeolites which are sometimes referred to as ZSM-5-type zeolites and which are described, for example, in U.S. Pat. Nos. 3,702,886 and U.S. Pat. No. Re. 29,948; 3,709,979; 3,832,449; 4,556,477; 4,076,842; 4,016,245; 4,046,859; 4,229,424; and 4,397,827 to which reference is made for details of these zeolites. These zeolites may be produced with differing silica:alumina ratios ranging from 12:1 upwards. They may, in fact, be produced from reaction mixtures from which aluminum is intentionally excluded, so as to produce materials having extremely high silica:alumina ratios which, in theory at least may extend up to infinity. Silica:alumina ratios of at least 30:1 and higher will be common for these zeolites, e.g., 70:1, 200:1, 500:1, 1600:1 or even higher. Highly siliceous forms of zeolites ZSM-5, ZSM-11 and ZSM-12 are described, respectively, in U.S. Pat. No. Re. 29,948 and European Patent Publication No. 14,059 to which reference is made for details of these zeolites. Also included herein is Zeolite Beta which has a Constraint Index in the range of approximately 0.6–2.0, and which is described in U.S. Pat. No. 3,308,069 and U.S. Pat. No. Re. 28,341.

A reaction mixture is prepared preferably containing an oxide of silicon, optionally an aluminum source, a templating agent which is an organic nitrogen containing compound, and an alkaline aqueous medium.

The sources of alkali metal oxide may be, for example, sodium, lithium, calcium, magnesium, cesium or potassium hydroxides, halides (e.g., chlorides, and bromides), sulfates, nitrates, acetates, silicates, aluminates, phosphates and salts of carboxylic acids.

The silicon oxide can be supplied from known sources such as silicates, silica hydrosol, precipitated silica hydrosol, precipitated silica, e.g., Hi-Sil, silica gel, silica acid. The aluminum oxide may be provided as only an impurity in another reactant, e.g., the silica source.

The sources of organic nitrogen-containing cations, depending, of course, on the particular zeolite product to result from crystallization from the reaction mixture, may be primary, secondary or tertiary amines or quaternary ammonium compounds. Non-limiting examples of quaternary ammonium compounds include salts of tetramethylammonium, tetraethylammonium, tetrapropylammonium, tetrabutylammonium, diethylammonium, triethylammonium, dibenzylammonium, dibenzyldimethylammonium, dibenzyldiethylammonium, benzyltrimethylammonium and chlorine. Non-limiting examples of amines useful herein include the compounds of trimethylamine, triethylamine, tripropylamine, ethylenedimine, propanediamine, butanediamine, pentanediamine, hexanediamine, methylamine, ethylamine, propylamine, butylamine, diamethylamine, diethylamine, dipropylamine, benzylamine, aniline, pyridine, piperidine and pyrrolidine.

In forming the films, a substrate is contacted with a chemical reaction mixture as described above capable of forming the desired zeolite and under crystallization conditions. After a period of time under suitable conditions, a cohesive film is formed adherent to the surface of the substrate. The orientation of the substrate surface in the reaction mixture is not critical, but it is preferably fully immersed in the synthesis solution, for a time greater than about 2 hours to about 1000 hours, preferably at least about 4.5 hours, more preferably from about 12 hours to about 120 hours; at a temperature of from about 50° C. to about 230° C., preferably from 100° C. to about 220° C.; and at a pressure from about 1 atmosphere to about 100 atmospheres, preferably from about 1 atmosphere to about 15 atmospheres.

The films are produced by synthesis under hydrothermal conditions on a substrate. Substrates contemplated to be used herein include, as non-limiting examples, metals such as Fe, Co, Ni, Sn, Ag, Pd, Pt, Cu and stainless steel, particular metals being Fe, Al, Cu, Ni and stainless steel; ceramics such as glass, clays (e.g., kaolinites, montmorillonites, and illites), quartz, mullite, titania, cordierite, zirconia, silica, alumina, spinel, carbides and nitrides (such as those of silicon, boron, zirconium, hafnium, tantalum, vanadium, molybdenum, tungsten, and niobium). It is not necessary, however, that the substrate contain silicon or aluminum.

The substrate may be an extruded monolith. Extruded monoliths of low surface area such as cordierite which may be in honeycomb shape, are advantageously used in emissions control from internal combustion engines. Other extruded monoliths of higher surface area such as titania, alumina, silica, zirconia and extruded zeolites are advantageously used in $NO_x$ emissions control such as in Selective Catalytic Reduction (SCR). Monoliths may also incorporate in their compositions, various inorganic additives such as glass particles, metal particles or diatomaceous earth. Further, the substrates may be wire, mesh or gauze.

The substrates may have various configurations. For example, the surface may be flat, curved, honeycomb shaped, layered plate form, etc.

The synthesis conditions for crystallization of a zeolite as adherent to a substrate may be further defined by a value d which is the ratio of the $YO_2$ or silica content of the synthesis hydrogel to the superficial surface area of the substrate (mg/cm²). The product zeolite film-coated substrate may be characterized by the zeolite loading, i.e., the amount of zeolite adhering to the surface, a value r (mg of zeolite/cm$^2$), and by the coating efficiency e, i.e., the ratio of the amount of zeolite adhering to the substrate to the amount of silica initially present in the crystallization mixture, wherein $e = r/d$ For maximum coating efficiency, d is less than 200, preferably between about 0.5 and about 200, more preferably in the range of about 2 to about 50; r is at least about 0.5, preferably about 1 to about 50; and e is at least about 0.05 preferably about 0.1 to about 1.0.

The zeolite coated substrates can be modified for a particular use by post synthesis treatment using well known techniques, in order to alter their catalytic and/or adsorption properties as desired for a particular application. For example, the structure can be steamed at a temperature of about 200° C. to 800° C. for about 1 to 50 hours. The structure can also be calcined.

Zeolites can be used either in the alkali metal form, e.g., the sodium or potassium form; the ammonium form; the hydrogen form or another univalent or multivalent cation form. When used as a catalyst the zeolite will be subjected to thermal treatment to remove part or all of the organic constituent. Aluminum may be incorporated into the zeolite framework by treatment with aluminum halide. The original alkali metal cations of the as synthesized zeolite can be replaced in accordance with techniques well known in the art, at least in part, by ion exchange with other cations. Preferred replacing cations include metal ions, hydrogen ions, hydrogen precursor, e.g., ammonium ions, and mixtures thereof. Particularly preferred cations are those which render the zeolite catalytically active, especially for hydrocarbon conversion. Replacing cations include hydrogen, rare earth metals and metals of Groups 3-12 of the Periodic Table of the Elements (New Notation, See, e.g., *CRC Handbook of Chemistry and Physics*, 69th Edition, CRC Press, Inc., (1988)).

A typical ion exchange technique would be to contact the synthetic zeolite with a salt of the desired replacing cation or cations. Examples of such salts includes the halides, e.g., chlorides, nitrates and sulfates.

The zeolite films described herein can be used as a catalyst in intimate combination with an oxidation-reduction component such as tungsten, vanadium, molybdenum, rhenium, copper, nickel, cobalt, chromium, manganese, or a noble metal such as platinum or palladium where a hydrogenation-dehydrogenation function is performed. Such component can be exchanged into the composition to the extent atom X, e.g., aluminum, is in the structure, impregnated in or on to it such as for example, by, in the case of platinum, treating the coated molecular sieve having ion exchange capacity with a solution containing a platinum metal-containing ion. Thus, suitable platinum compounds include chloroplatinic acid, platinous chloride and various compounds containing the platinum amine complex.

The metal containing zeolite film structures may have essentially no acid activity, or they may have substantial acid activity to provide for dual functional catalysis. The catalytic activity of the structures can be adjusted from essentially zero to high activity, depending on the particular use thereof.

Zeolites can be acidic or non-acidic, depending on the framework aluminum content and on the amount of compensating cations, such as Na+, K+, etc. The compositions comprising a dehydrogenation metal combined with a non-acidic zeolite do not exhibit any appreciable acid activity. These catalysts would meet the criteria of non-acidic catalysts described by Davis and Venuto, *J. Catal.* 15, 363 (1969). Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%. Alternatively, the non-acidic compositions will exhibit a pH of at least 6 when added to distilled deionized pH 7 water maintained under inert (such as argon) atmosphere; by an inert atmosphere in this context it means an atmosphere free of $CO_2$. Typically, in these tests, 100 mg of catalyst was added to 30 ml. of distilled deionized water. Some compositions will exhibit a pH of at least 7.5.

In non-acidic zeolite materials, all cation-exchangeable sites are occupied by non-hydrogen (non-proton) and by non-hydrogen precursors, such as $NH_4^+$. Specifically such sites are occupied by Na+, K+, Cs+ or admixtures thereof. The alkali metals serve to neutralize any acidity due to framework aluminum. The source of alkali metal cation can derive from cations incorporated during synthesis, in excess of the aluminum content thereof. Conventional dealumination including steam treatment and aqueous acid treatment may be used to remove some of the aluminum from the crystal framework. The final product may be treated with a basic solution of an alkali metal hydroxide, carbonate or bicarbonate as a final step prior to use, as described for example in U.S. Pat. No. 4,652,360, which is incorporated herein by reference.

The zeolite film coated substrates of the present invention, when employed either as an adsorbent or as a catalyst in an organic compound conversion process should usually be dehydrated, at least partially. This can be done b heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing the bonded molecular sieve in a vacuum, but a longer time is required to obtain a sufficient amount of dehydration.

The zeolite coated substrate has sorption affinity for hydrocarbons and catalytic activity for many uses, particularly in removing atmospheric pollutants from industrial exhaust gases, and hydrocarbon conversion processes.

The term industrial exhaust gas as used herein means any waste gas which is formed in an industrial process or operation and which is normally disposed of by discharge to the atmosphere. The composition of such a gas varies and depends on the particular process or operation which leads to its formation. When formed in the combustion of fossil fuels, it will generally contain oxygen, nitrogen, steam, carbon dioxide, carbon monoxide, unburned hydrocarbons especially olefins and aromatics resulting from incomplete combustion, and $NO_x$ as relatively low levels, such as up to about 1000 ppm of nitric oxide plus nitrogen dioxide Sulfur-containing fuels will produce an exhaust gas that contains some $SO_x$ including sulfur dioxide and sulfur trioxide.

Industrial exhaust gases include flue gases produced, for example, by incinerators, turbines, $HNO_3$ plants, coal-fired and fossil-fueled power plants, and internal combustion engines. Methods of removal of the pollutants include catalytic oxidation, e.g., of unburned hydrocarbons and carbon monoxide, reduction of $NO_x$ and adsorption or absorption of hydrocarbons and $SO_x$.

Examples of particular applications of the inventive structure include removal of unburned hydrocarbons such as $C_3$–$C_6$ paraffins and olefins, and aromatics, from cold engine flue gas using the hydrogen or alkali metal ion exchanged substrate, which may be impregnated with oxidation metal components including, for example, Pt, Cu, Ni and V; removal of noxious $NO_x$ gas from hot engine flue gas and Selective Catalytic Reduction (SCR) of NO with $NH_3$ in gases from FCC catalyst regenerators or power plants using, for example, copper, iron, noble metals or other transition elements ion exchanged or impregnated into the zeolite film on monoliths; dehydrogenation of alkanes to alkenes, e.g., isobutane to isobutene, using, for example, noble metal containing zeolite films of high $SiO_2/Al_2O_3$ molar ratio on cordierite, silica or titania monoliths.

A preferred catalyst composition according to the present invention particularily useful in equilibrium limited dehydrogenation of light paraffins comprises a non-acidic ZSM-5 film. The use of a dehydrogenation metal containing non-acidic ZSM-5 coated substrate will result in lower process pressure and higher paraffin conversion. The light paraffins include alkanes of 2 to 5 carbon atoms such as ethane, propane, butane, isobutane, pentane and isopentane. Dehydrogenation of those respective alkanes will yield ethylene, propylene, butene, isobutene, pentene and isopentene.

It is believed that the paraffin dehydrogenation reaction is equilibrium limited when carried out in a conventional reactor due to relatively high hydrogen partial pressure. For equilibrium limited paraffin dehydrogenation processes, the reactor pressure must be kept to a minimum, otherwise the attainable equilibrium conversion may be reduced. As a result, equilibrium catalysts are often designed as extrudates to minimize the pressure drop across the reaction bed.

Arranging the non-acidic ZSM-5 coated substrates in the dehydrogenation reactor will result in lower process pressure due to the lack of pressure drop across the reactor. The attainment of lower process pressure results in higher paraffin conversion.

The amount of dehydrogenation metal in the non-acidic ZSM-5 film employed can range from about 0.01 to about 30 weight percent and preferably 0.1 to about 10 weight percent of the zeolite material.

In a preferred embodiment, the non-acidic Pt/ZSM-5 of the invention is prepared by treating with $Pt(NH_3)_4Cl_2$ in aqueous solution to incorporate the necessary platinum into the catalyst composition formulation followed by base treatment with an alkali metal hydroxide.

In a further embodiment, the dehydrogenation metal-containing non-acidic film of interconnected zeolite crystals having the structure of ZSM-5 can contain a modifier selected from the group consisting of tin, indium, thallium, lead, and sulfur. The use of a modifier in a dehydrogenation metal containing non-acidic crystalline material is described in U.S. Pat. No. 4,990,710, incorporated herein by reference.

The modifier content of the zeolite can range from 0.01 to 20 weight percent. Practically, the modifier content will range from 0.1 to 10 weight percent.

The light paraffin dehydrogenation is suitably carried out under paraffin dehydrogenation conditions which include pressures varying from subatmospheric, to greater than atmospheric. Preferred pressures range from 0.1 to 30 psig. However, pressures up to 100 psig may be employed. The dehydrogenation is conducted at elevated temperatures ranging from 300° C. to 700° C. and most preferably from 400° C. to 600° C. Reactor inlet $H_2$/feed ratios are 5 or less; even at reactor inlet ratios of zero(0), there will be a hydrogen partial pressure in the reactor because hydrogen is a byproduct of dehydrogenation. The weight hourly space velocity is 0.1 to 50, preferably 0.5 to 10.

Dehydrogenation may be conducted in the presence or absence of added hydrogen and in the presence of diluents inert to conditions of the paraffin dehydrogenation such as nitrogen and methane.

According to these applications, the catalytic compositions of matter according to the present invention may also be used for selective conversion of inorganic compounds such as oxides of nitrogen ($NO_x$), for example, industrial exhaust gases and the gases formed during the oxidative regeneration of catalysts used in the processing of hydrocarbons, especially in catalytic cracking operations. The zeolite is preferably at least partly in the hydrogen form, but it may advantageously contain a minor amount of noble metal as a catalytic component, especially a metal of Periods 4, 5 and 6 and Groups 8–11 of the Periodic Table, especially Fe, Co, Ni, Cu, Rh, Pd, Ag, Ir, Pt or mixtures thereof. Amounts of metal up to about 1 weight percent are typical with lower amounts, e.g., up to about 0.1 or 0.5 weight percent being preferred.

The $NO_x$ reduction is suitably conducted by passing the gas containing the oxides of nitrogen over the catalyst at an elevated temperature, typically at least about 200° C., and usually within the range of about 200 to about 600° C. The gas mixture may be mixed with, for example, ammonia to promote reduction of the oxides of nitrogen and pre-mixing may be conducted at a temperature of up to about 200° C. The amount of ammonia which is mixed with the gas mixture is shown by the equations:

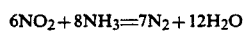

$6NO_2 + 8NH_3 = 7N_2 + 12H_2O$

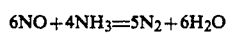

$6NO + 4NH_3 = 5N_2 + 6H_2O$

For the selective catalytic reduction (SCR) of $NO_x$ in industrial exhaust gases, the reduction proceeds approximately according to the equations (1) and (2):

$$2\ NO_2 + 4NH_3 + O_2 \xrightarrow{\text{catalyst}} 3N_2 + 6H_2O \quad (1)$$

$$4\ NO + 4NH_3 + O_2 \xrightarrow{\text{catalyst}} 4N_2 + 6H_2O \quad (2)$$

The structures of the invention may also be used for the reduction of oxides of nitrogen in gaseous mixtures in the presence of other reducing agents such as carbon monoxide and hydrocarbon. Reduction of the oxides of nitrogen in this way is of particular utility in the regeneration of fluid catalytic cracking (FCC) catalysts, and in $NO_x$ emission control from automotive internal combustion engines since regeneration under appropriate conditions will produce the required concentrations of carbon monoxide and hydrocarbon which may then be used to reduce the proportion of $NO_x$ in the effluent gases in the presence of the catalyst.

The structures of the invention may also be used for the removal of both $NO_X$ and $SO_X$ from a typical flue gas stream. The removal of $SO_X$ is suitably conducted by passing the gas containing the oxides of both elements over the structure at a temperature higher than 200° C. Premixing the flue gas stream with, for example, hydrogen promotes the reduction of the oxides of sulfur and nitrogen according to the equation:

$$SO_2 + 2NO + 5H_2 \rightarrow H_2S + N_2 + 4H_2O$$

The activity of the film is an important consideration in acid-type catalysis. Activity may be correlated with acid character. Silicious zeolites may be considered to contain $SiO_4$-tetrahedra. Substitution by a trivalent element such as aluminum introduces a negative charge which must be balanced. If this is done by a proton, the material is acidic. The charge may also be balanced by cations exchange with alkali or alkaline earth metal cations.

One measure of catalytic activity may be termed the Alpha Value. The Alpha Value is an approximate indication of the catalyst acid activity and it gives the relative rate constant (rate of normal hexane conversion per volume of catalyst per unit time). It is based on the activity of the highly active silica-alumina cracking catalyst taken as an Alpha of 1 (Rate Constant=0.016 $sec^{-1}$). The Alpha Test is described in U.S. Pat. No. 3,354,078, in the *Journal of Catalysis*, Vol. 4, p. 527 (1965); Vol. 6, p.278 (1966); and Vol. 61, p.395 (1980), each incorporated herein by reference as to that description. The experimental conditions of the test used herein include a constant temperature of 538° C. and a variable flow rate as described in detail in the *Journal of Catalysis*, Vol. 61, p.395 (1980).

The crystalline films of the present invention are readily convertible to catalytically active material for a variety of organic, e.g., hydrocarbon, compound conversion processes. Such conversion process include, as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0.1 $hr^{-1}$ to about 20 $hr^{-1}$; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 300° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatic, e.g., benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g., methanol, or ethers, e.g., dimethylether, or mixtures thereof to hydrocarbons including olefins and/or aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure from about atmospheric to about 60 atmospheres and a weight hourly space velocity of from about 0.08 to about 20; alkylating aromatic hydrocarbons, e.g., benzene and alkylbenzenes in the presence of an alkylating agent, e.g., olefins, formaldehyde, alkyl halides and alcohols, with reaction conditions including a temperature of from about 250° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

In general, therefore, catalytic conversion conditions over a catalyst comprising the zeolite film structure in active form include a temperature of from about 100° C. to about 760° C., a pressure of from about 0.1 atmosphere (bar) to about 200 atmospheres (bar), a weight hourly space velocity of from about 0.08 $hr^{-1}$ to about 2000 $hr^{-1}$ and a hydrogen/organic, e.g., hydrocarbon compound of from 0 to about 100.

The films can also be used as adsorbents and separation vehicles in fine chemical applications. At least one component in a mixture of components can be partially or substantially separated from a mixture of components having differential sorption characteristics with respect to the zeolite film by contacting the mixture with the film to selectively sorb the one component. Examples of this include contacting a mixture comprising water and at least one hydrocarbon component, whereby at least one hydrocarbon component is selectively sorbed. Another example includes sorption of at least one hydrocarbon component from a mixture comprising same and at least one additional hydrocarbon component.

In order to more fully illustrate the nature of the invention and the manner of practicing same, the following examples are presented.

EXAMPLES 1-18

The following substrates were prepared:
(a) Pyrex glass plate (Corning Glass Works, Corning, N.Y.)
   4 cm×3 cm×0.4 cm
(b) Cordierite Monolith (Corning Glass Works, Corning, N.Y.)
   cylindrical, diameter=one inch
   height=one inch, 100 cells/sq.inch
(c) Cordierite Monolith (Corning Glass Works, Corning, N.Y.)
   cylindrical, diameter=one inch
   height=one inch, 400 cells/sq.inch
(d) Mullite Monolith (Corning Glass Works, Corning, N.Y.)

cylindrical, diameter = one inch
height = one inch, 100 cells/sq. inch

From the geometry of the monolith substrates, the surface area available for coating with zeolite was estimated to be about 170 cm² for substrates b and d and about 360 cm² for substrate c.

A synthesis hydrogel was prepared consisting of varying amounts of distilled water, NaOH, tetrapropylammonium bromide (TPABr) colloidal silica (Ludox AS-40) and NaAlO₂. First a solution was prepared by dissolving varying quantities of NaOH, TPABr and NaAlO₂ in distilled water under stirring. The colloidal silica sol was added to the basic solution and the final hydrogel stirred to produce a homogeneous solution. The substrates a,b,c,d were separately calcined in air, cooled, weighed and suspended vertically in the center of 125 ml tetrafluoroethylene (Teflon) non-stirred autoclaves so that the external surfaces of the substrates were oriented vertically. The vertical orientation was chosen to minimize gravitational deposition of homogeneously nucleated crystals (i.e., crystals not bonded to the substrate). The substrate was also not in contact with the bottom of the autoclave. The prepared synthesis hydrogel was poured into the vessel until the substrate was fully immersed, the autoclave sealed and placed inside a preheated convection oven. The autoclave was removed from the oven after a specified time period, the substrate removed from the solution, washed under flowing distilled water, dried, calcined and weighed. The weight of each substrate was higher than its weight before synthesis due to film deposition. The presence of a ZSM-5 film was confirmed by x-ray diffraction and Scanning Electron Microscopy (SEM). The results are summarized in Table I below.

In the Table, the composition of the synthesis hydrogel is defined by $SiO_2/Al_2O_3$ $H_2O/SiO_2$ $OH^-/SiO_2$ $TPABr/SiO_2$ The synthesis conditions are defined by
synthesis temperature, T (°C.)
crystallization time, t (days)

the ratio of the silica content of the synthesis hydrogel to the substrate superficial surface area, d (mg/cm²).

The coated monolith is characterized by
zeolite loading, r (mg of zeolite/cm²)
coating efficiency, e (mg of zeolite on substrate/mg of silica initially present in solution)

$e = r/d$

Figure 2:
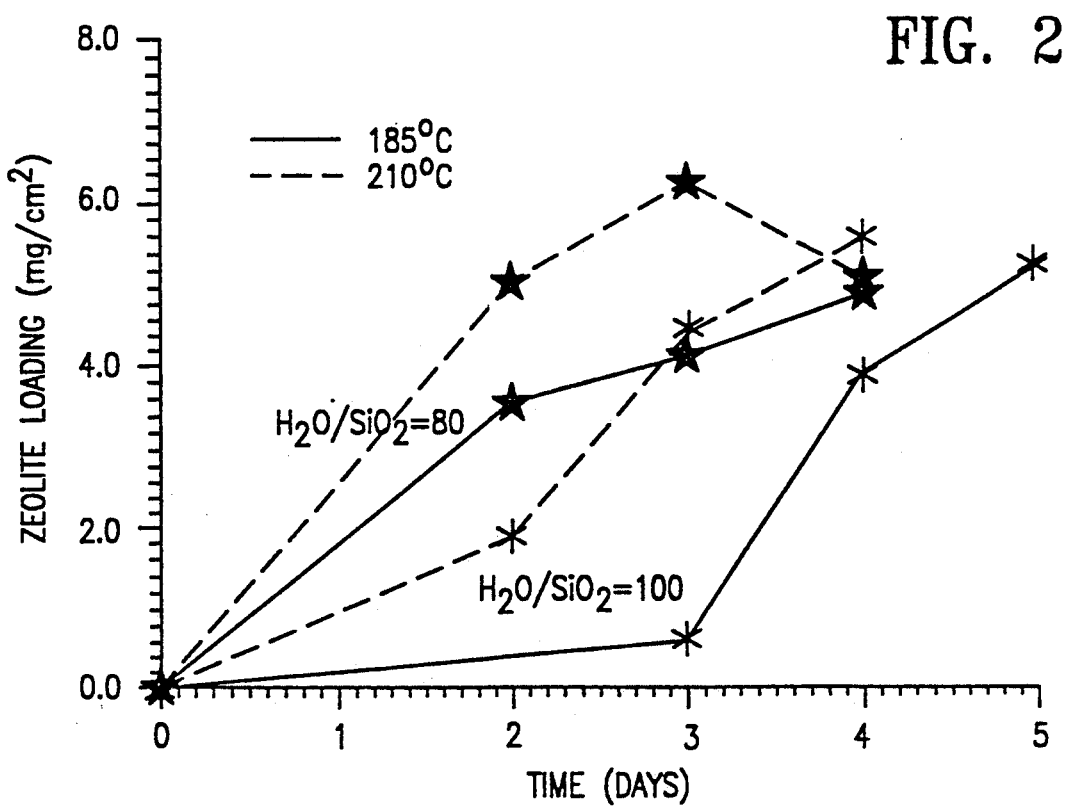
FIG. 2 is a graph representing zeolite loading on monoliths after various times at two temperatures and two $H_2O/SiO_2$ values.
Figure 3:
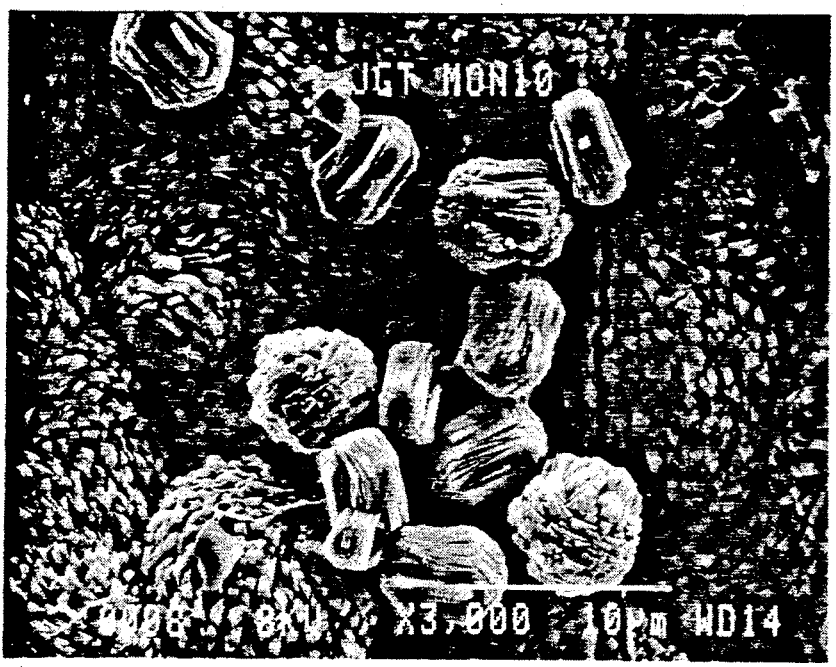
FIG. 3 is a Scanning Electronic Microscope (SEM) photomicrograph of the surface morphology of the bonded zeolite of example 11 at 3,000 magnification.
Figure 4:
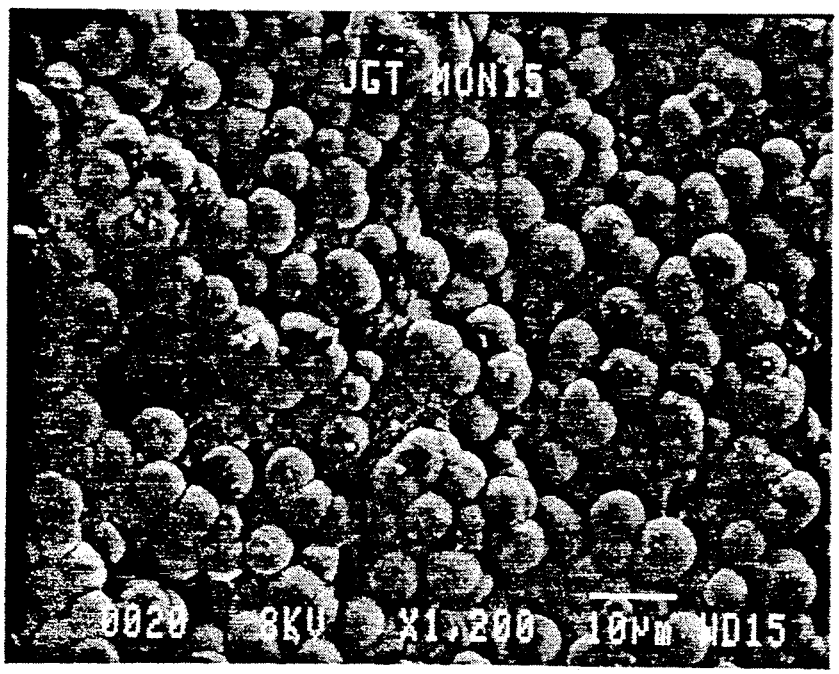
FIG. 4 is a SEM photomicrograph of the surface morphology of the bonded zeolite of example 16 at 1,200 magnification.

The process conditions and results are summarized in Table I. Selected synthesis conditions are graphed in FIGS. 1 and 2. SEM of the films of Examples 11 and 16 is shown in FIGS. 3 and 4 respectively.

TABLE I

| Ex | $SiO_2/Al_2O_3$ | $H_2O/SiO_2$ | $OH^-/SiO_2$ | $TPABr/SiO_2$ | Subst. | T | t | d | r | e |
|---|---|---|---|---|---|---|---|---|---|---|
| 1 | ∞ | 30.0 | 0.025 | 0.055 | (a) | 180 | 3.0 | 460.0 | 46.0 | 0.10 |
| 2 | 80 | 100.0 | 0.10 | 0.10 | (a) | 180 | 5.0 | 63.0 | 15.1 | 0.24 |
| 3 | 80 | 30.0 | 0.025 | 0.055 | (a) | 180 | 3.0 | 460.0 | 0.0 | 0.00 |
| 4 | ∞ | 30.0 | 0.025 | 0.055 | (c) | 180 | 3.0 | 31.0 | 24.2 | 0.78 |
| 5 | ∞ | 30.0 | 0.025 | 0.055 | (b) | 180 | 1.0 | 18.0 | 11.5 | 0.64 |
| 6 | 400 | 30.0 | 0.025 | 0.055 | (c) | 180 | 3.0 | 31.0 | 19.5 | 0.63 |
| 7 | 150 | 50.0 | 0.065 | 0.075 | (b) | 180 | 5.0 | 32.0 | 9.6 | 0.30 |
| 8 | 100 | 100.0 | 0.10 | 0.10 | (c) | 180 | 8.0 | 8.5 | 6.55 | 0.77 |
| 9 | 100 | 100.0 | 0.10 | 0.10 | (c) | 180 | 5.0 | 50.0 | 11.0 | 0.22 |
| 10 | 100 | 100.0 | 0.10 | 0.10 | (b) | 180 | 5.0 | 95.0 | 6.65 | 0.07 |
| 11 | 100 | 100.0 | 0.10 | 0.10 | (b) | 180 | 9.0 | 16.0 | 7.36 | 0.46 |
| 12 | 100 | 100.0 | 0.10 | 0.10 | (d) | 180 | 9.0 | 16.0 | 8.64 | 0.54 |
| 13 | 80 | 100.0 | 0.10 | 0.10 | (b) | 180 | 1.7 | 16.0 | 0.48 | 0.03 |
| 14 | 80 | 100.0 | 0.10 | 0.10 | (b) | 180 | 3.0 | 16.0 | 1.12 | 0.07 |
| 15 | 80 | 100.0 | 0.10 | 0.10 | (b) | 180 | 4.0 | 16.0 | 1.60 | 0.10 |
| 16 | 80 | 100.0 | 0.10 | 0.10 | (b) | 180 | 5.0 | 16.0 | 6.40 | 0.40 |
| 17 | 80 | 100.0 | 0.10 | 0.10 | (d) | 180 | 5.0 | 16.0 | 5.76 | 0.36 |
| 18 | 80 | 20.0 | 0.10 | 0.10 | (b) | 180 | 5.0 | 40.0 | 1.20 | 0.03 |

All substrates, except in examples 3 and 18, were coated with a uniform layer of ZSM-5 which constituted from 2.4 to 179% of the substrate weight. Except for examples 3 and 18, solid particles in powder form were not observed, but only zeolite films coating the substrate and internal vessel walls were observed.

Under the conditions of the invention, the weight of the zeolite film is maximized and the crystallization of homogeneously nucleated crystals is minimized. When the H₂O/SiO₂ ratio was outside the parameters of the invention as shown in comparative example 18, homogeneously nucleated crystals which were not adherent to the substrate were formed. Furthermore, in Example 18, the zeolite loading of the monolith (r=1.2 mg/cm²) and the coating efficiency (e=0.03) were much lower than the zeolite loading and coating efficiency attained under the synthesis conditions of the invention.

In general, the coating efficiency is less than 1.0 because at the end of the crystallization period, some silica may have remained in solution, coated the internal walls of the vessel or have formed homogeneously nucleated crystals which settled at the bottom of the synthetic vessel. This homogeneous nucleation is minimized under the conditions of the invention.

EXAMPLE 19

Acid Activity

The acid activities of the uncoated cordierite and mullite samples were determined by the well known hexane cracking test (alpha test). The uncoated monoliths were found to have no acid activity (alpha=0)

The structures of Examples 11, 15 and 16 were calcined in air at 538° C. for 6 hours, and ion exchanged according to known procedures. The alpha values of these samples were determined as follows:

| Example | Alpha |
| --- | --- |
| 11 | 44.0 |
| 15 | 4.0 |
| 16 | 27.0 |

The above data clearly demonstrate that the deposited zeolite films have appreciable hexane cracking activity. Hence, these monoliths can be used as catalysts in a variety of hydrocarbon conversion reactions.

EXAMPLE 20

Selective Catalytic Reduction (SCR) of NO with $NH_3$

The cylindrical monoliths of Examples 9 and 12 were inserted into a quartz reactor tube having an inside diameter which was the same as their outside diameter. Quartz wool was used to fill around the edges to prevent gases from bypassing the monolith cells. The following table summarizes the results obtained on these materials.

| Coated Monolith | $NO_x$ Conversion, % | | |
| --- | --- | --- | --- |
| | 350° C. | 450° C. | 550° C. |
| Ex. 9 | 28 | 41 | 62 |
| Ex. 12 | 7 | 19 | 35 |

These results show that catalysts prepared according to the invention can be used in Selective Catalytic Reduction.

EXAMPLE 21

Adsorption of Hydrocarbons from Exhaust Flue Gas

The cylindrical monolith of example 4 is inserted into a quartz reactor tube having an inside diameter of 1 inch. The monolith is calcined in air at 540° C. for four hours and cooled to 90° C. in nitrogen. A gas stream containing 1500 ppm propylene, in nitrogen is blown through the channels of the monolith at 400 cc/min for 30 minutes. The effluent gas stream is collected and analyzed for hydrocarbon content, which is 150 ppm propylene, i.e., smaller than the inlet concentration, due to adsorption and retention of p-xylene by the zeolite film.

EXAMPLE 22

Removal of p-Xylene Impurity from m-Xylene

The cylindrical monolith of example 4 is calcined in air at 540° C. for four hours and cooled to room temperature in dry helium. It is then contacted for 10 minutes with 10 g of m-xylene which contains 1 wt% p-xylene as an impurity. After contact, the p-xylene impurity content of the liquid is 0.2% due to selective adsorption of p-xylene by the structure.

EXAMPLE 23

Dehydrogenation of Paraffins

The structures of Examples 1, 4 and 5 are calcined in air at about 540° C. The calcined ZSM-5 coated substrates are stirred in an aqueous solution of $Pt(NH_3)_4Cl_2$ containing 1-2 grams per 100 grams ZSM-5. The Pt/ZSM-5 coated substrates are then calcined in air at 350° C.

The structures of Examples 1, 4 and 5 may also be modified with tin, indium, thallium or lead by adding soluble salts, such as tin sulfate, to the ZSM-5 synthesis gel prior to coating the substrates.

Additional base treatment of the calcined Pt/ZSM-5 substrates may be used for the purpose of reducing the acidity. The calcined Pt/ZSM-5 substrates are impregnated with basic salts, such as $Cs_2CO_3$, $CsHCO_3$ and CsOH, to provide 0.5-10% Cs on a zeolite basis. Sodium, potassium, calcium and magnesium salts are also effective. The base treated Pt/ZSM-5 substrates are then calcined at 500° C. prior to use.

Isobutane is passed over the non-acidic Pt/ZSM-5 substrate catalyst at 650° C. and atmospheric pressure at a WHSV of 2-30 $hr^{-1}$ based on zeolite content. Isobutene yields of 30-40% are obtained.

Changes and modifications in the specifically described embodiments can be carried out without departing from the scope of the invention which is intended to be limited only by the scope of the appended claims.

What is claimed is:

1. A process for converting feedstock organic compounds to conversion products which comprises passing said feedstock into a reaction zone which contains a catalytically active structure comprising a film of interconnected zeolite crystals bonded to a substrate surface;
   wherein said catalytically active structure is prepared by a process comprising contacting the substrate with a crystallization reaction mixture capable of forming the zeolite;
   and wherein said crystallization reaction mixture comprises a $H_2O/YO_2$ molar ratio of at least about 25 when the reaction mixture has a $YO_2/X_2O_3$ ratio of greater than about 400, a $H_2O/YO_2$ molar ratio of at least about 35 when the $YO_2/X_2O_3$ ratio is greater than about 150 and less than about 400, and a $H_2O/YO_2$ molar ratio of at least about 45 when the $YO_2/X_2O_3$ ratio is less than about 150; and Y is a tetravalent element and X is a trivalent element.

2. The method of claim 1 wherein the zeolite has a Constraint Index from about 1 to about 12.

3. The method of claim 1 wherein the zeolite demonstrates an x-ray diffraction pattern selected from the group consisting of ZSM-5, ZSM-11, ZSM-12, ZSM-22, ZSM-23, ZSM-35, ZSM-38, ZSM-5/ZSM-11 intermediate, ZSM-48 and Zeolite Beta.

4. The process of claim 1 wherein the feedstock organic compounds are hydrocarbons.

5. The process of claim 1 wherein the process is dehydrogenation of alkanes.

6. A process for the dehydrogenation of light paraffins which comprises contacting a hydrocarbon feedstream comprising $C_2$ to $C_5$ paraffins under dehydrogenation conditions in a reaction zone with a catalyst composition comprising a dehydrogenation metal-containing non-acidic film of interconnected zeolite crystals having the structure of ZSM-5 bonded to a substrate surface, wherein the film bonded to the substrate surface is prepared from a reaction mixture comprising an $H_2O/YO_2$ ratio of at least about 25 when the reaction mixture has a $YO_2/X_2O_3$ ratio of greater than about 400, a $H_2O/YO_2$ molar ratio of at least about 35 when the $YO_2/X_2O_3$ ratio is greater than about 150 and less than about 400, and a $H_2O/YO_2$ molar ratio of at least about 45 when the $YO_2/X_2O_3$ ratio is less than about 150; and Y is a tetravalent element and X is a trivalent element.

7. The process of claim 6 wherein said substrate is an extruded monolith.

8. The process of claim 6 wherein said substrate is selected from the group consisting of cordierite, silica and titania.

9. The process of claim 6 wherein said hydrocarbon feedstream comprises isopentane.

10. The process of claim 6 wherein said hydrocarbon feedstream comprises propane.

11. The process of claim 6 wherein said hydrocarbon feedstream comprises isobutane.

12. The process of claim 6 wherein said dehydrogenation metal is platinum.

13. The process of claim 6 wherein the zeolite having the structure of ZSM-5 contains a modifier, and wherein said modifier is selected from the group consisting of tin, indium, gallium, lead, thallium, and sulfur.

14. The process of claim 6 wherein said modifier is in an amount in the range of from about 0.01 to about 20 weight percent of the catalyst film composition.

15. The process of claim 6 wherein said dehydrogenation conditions include a temperature in the range of from about 300 to about 700° C. and a pressure in the range of below about 30 psig.

16. The process of claim 6 wherein said dehydrogenation metal is an amount in the range of from about 0.01 to about 30 weight percent.

* * * * *